United States Patent [19]

Hiranuma et al.

[11] Patent Number: 4,969,817
[45] Date of Patent: Nov. 13, 1990

[54] ARTIFICIAL TEETH

[75] Inventors: Kenji Hiranuma, Nagoya; Hiroshi Mori, Chita; Akira Hasegawa, Inuyama; Ikuo Ikeda, Nagoya, all of Japan

[73] Assignee: G-C Toshi Kogyo Corporation, Kasugai, Japan

[21] Appl. No.: 251,880

[22] Filed: Sep. 30, 1988

[30] Foreign Application Priority Data

Oct. 2, 1987 [JP]   Japan ................................ 62-249385

[51] Int. Cl.$^5$ ............................................ A61C 13/08
[52] U.S. Cl. ................................ 433/202.1; 433/212.1
[58] Field of Search ................... 433/202.1, 206, 212.1, 433/196, 197, 204

[56] References Cited

U.S. PATENT DOCUMENTS 1,380,819  6/1921  Marriott .............................. 433/206
4,523,912  6/1985  Breustedt et al. ................. 433/202.1
4,795,345  1/1989  Ai et al. ............................ 433/202.1

Primary Examiner—Cary E. Stone
Attorney, Agent, or Firm—Oblon, Spivak, McClelland, Maier & Neustadt

[57] ABSTRACT

An artificial tooth has a basal plane in which an areal ratio of a labial or buccal subplane to a lingual subplane is in a range of 10:1 to 1:10, and an angle that both subplanes make with a dental axis, i.e., an angle of retention, assumes a concave shape and is in a range equal to or larger than 45° to less than 180°. A retaining hole can be provided in the basal plane of the artificial tooth so as to further improve its performance.

18 Claims, 3 Drawing Sheets

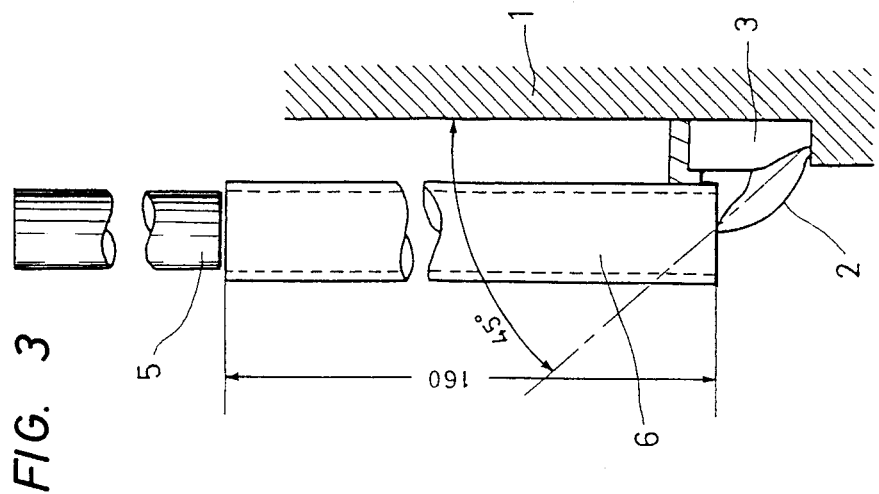
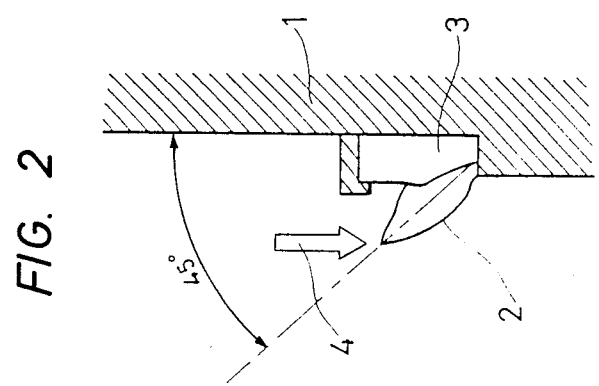
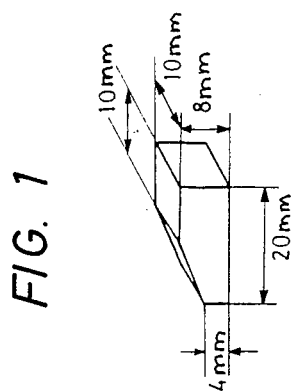
FIG. 1
FIG. 2
FIG. 3

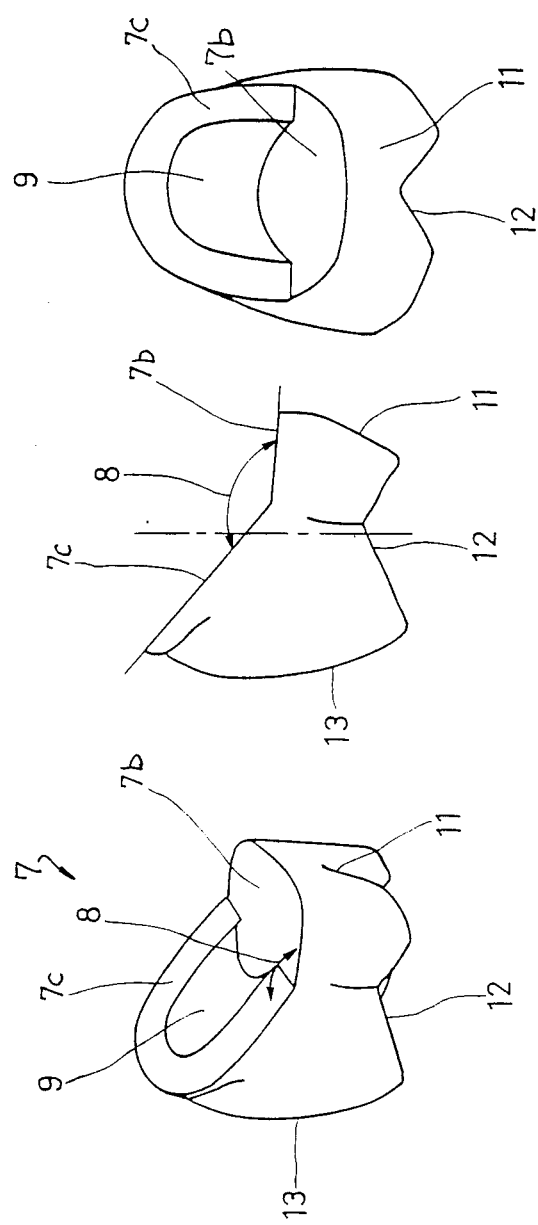

ARTIFICIAL TEETH

BACKGROUND OF THE INVENTION

1. Field of the Invention

The present invention relates to the geometry of artificial teeth for front-and molar-tooth portions, which are formed of a synthetic resin or a composite material of synthetic resins and ceramics, and have an angle of retention formed to their basal planes.

2. Description of the Prior Art

Heretofore, a number of geometries have been imparted to the basal planes of artificial teeth so as to augment their bonding strength with respect to plate resins. Until now undercuts or retaining pins have been used for ceramic artificial teeth in particular, because they should always be retained by means of a mechanical retaining force due to the fact that they show no scientific bond strength with respect to plate resins whatsoever. As regards artificial teeth formed of a synthetic resin or a composite material of synthetic resins and ceramics, however, some scientific bonding strength may be expected with respect to plate resins, since they are formed of the same polymethyl methacrylate or its derivative as the plate resins. For that reason, the geometries of the basal planes of artificial teeth have not received attention at all, or even if some consideration has been given thereto, such geometries have had little effect in increasing their bonding strength with respect to plate resins. Referring to the geometries of the basal planes to which a significant attempt has been made in the art to increase the bonding strength between artificial teeth and plate resins, there have been only two methods; one for increasing the surface area of the basal planes and the other for adding a simple retaining hole thereto.

Thus, only three geometries, i.e., (1) a flat plane, (2) a plane curved to increase its surface area and (3) a plane having a simple retaining hole in it, have been available for the basal planes of artificial teeth.

The bonding strength between artificial teeth and plate resins plays an important role in the following five possible cases:

(1) Preparation of a denture (e.g., gypsum-indexing), (2) Mastication with a denture put in the mouth (lateral, anterior/posterior and vertical movements of the jaws), (3) Repair of a denture (especially, polishing for the occlusal equilibration of artificial teeth), (4) Mishandling of a denture in use (dropping or treading), and (5) Implantation of artificial teeth in a temporary fitting wax, when carrying out their try-in-the-mouth operation before preparing a denture.

Of these, cases (1) to (4) correlate to a bonding strength with respect to plate resins after polymerization, and case (5) relates the ease with which artificial teeth are implanted in a temporary fitting wax (for a instance, G-C Utility Wax) for a try-in-the-mouth operation and involves danger resulting from the disengagement of artificial teeth in the mouth.

The basal planes of artificial teeth so far available assume the following three possible geometries:

(1) a flat plane, (2) a plane curved to increase its surface area, and (3) a plane having a simple retaining hole in it.

In the five cases as mentioned above, these geometries are all insufficient in the bonding strength between artificial teeth and plate resins for the reasons which will be summarized just below.

(1) when preparing a denture, artificial teeth disengage from a plate resin. If the basal plane of an artificial tooth is flat, then not only does it have a limited surface area, but it is also only resistive to a simple tensile force and is ineffective with respect to a shearing force. If the basal plane of an artificial tooth is therein provided with a simple retaining hole, then a portion of the hole receiving a plate resin becomes a notch on which stress concentrates, thus leading to breaking of the plate resin. If the basal plane of an artificial tooth formed of a synthetic resin or a composite material of synthetic resin and ceramics is curved, then any artificial toothretaining effect is not expected, however much that plane is curved so as to increase its surface area due to a cross-linking agent being used for the most part therein.

(2) Since complicated movements are repeated by mastication in the mouth, stress is applied on the interface of a denture and a plate resin by lateral, anterior/posterior and vertical movements of the jaws, although gradually, with the result being that the denture is very much fatigued. The flat, curved and holed (for simple retaining) geometries of the basal planes so far available are not at all effective for such three-dimensional application of loads.

(3) After a denture has been put in the mouth and used over an extended period, it must necessarily be repaired. That is, artificial teeth should often be either polished with a carbon random point or anything similar or automatically milled-in with G-C lapping paste on an articulator. In such cases, interfacial breaking of the artificial teeth and a plate resin, due to fine vibrations of the point, is caused and proceeds so rapidly that the flat, curved and holed (for simple retaining) geometries of the basal planes often result in disengagement of the artificial teeth from the plate.

(4) The gravest problem with the use of dentures is inadvertant mishandling by patients themselves. For instance, the disengagement of artificial teeth from the associated plate is most frequently caused, when the dentures are dropped or trod upon with a large force. In such a case, the dentures receive an impact force, and so should possess bond strength toughness. However, the flat, curved and holed (for simple retaining) basal planes so far available cannot stand up to such an impact force.

(5) Before preparing a denture, the form and color tone of artificial teeth are selected. The thus selected suitable artificial teeth should then be implanted in a temporal fitting wax (for instance, G-C Utility Wax), which is to be tried in the mouth. However, artificial teeth which have their basal planes flattened, curved or holed for simple retaining cannot be temporally fitted to the wax in a satisfactory manner. In addition, such artificial teeth are very dangerous due to the fear that during a tri-in-the-mouth operation, they may disengage from the wax and block the throat or the bronchus, ending in suffocation.

SUMMARY OF THE INVENTION

As a result of intensive studies made to solve such problems as mentioned above, it has been found that they can be solved by the provision of an artificial tooth having a basal plane in which an areal ratio of a labial or buccal subplane to a lingual subplane is in a range of 10:1 to 1:10, and an angle between the labial or buccal subplanes and a lingual subplane, i.e., an angle of retention, assumes a concave shape and is an angle equal to or larger than 45° and less than 180°. It has also been found that a retaining hole can be provided in such an artificial tooth so as to further improve its performance.

BRIEF DESCRIPTION OF THE DRAWINGS

The present invention will now be explained specifically but not exclusively with reference to the accompanying drawings, in which:

FIG. 1 illustrates a wax model for making a test sample for carrying out bond testing with an artificial tooth and a plate resin according to Japan Dental Materials Association Standards (JDMAS), FIG. 2 illustrates a test sample-fixing instrument used for conducting bond testing with an artificial tooth and a synthetic resin, a fixing procedure and a direction of the application of a load, FIG. 3 illustrates a jig for determining impact bond strength between an artificial tooth and a plate resin, FIG. 5 illustrates the maxillary left-primary molar of the artificial teeth for a molar-tooth portion according to the present invention.

DESCRIPTION OF THE PREFERRED EMBODIMENT

Figure 4:
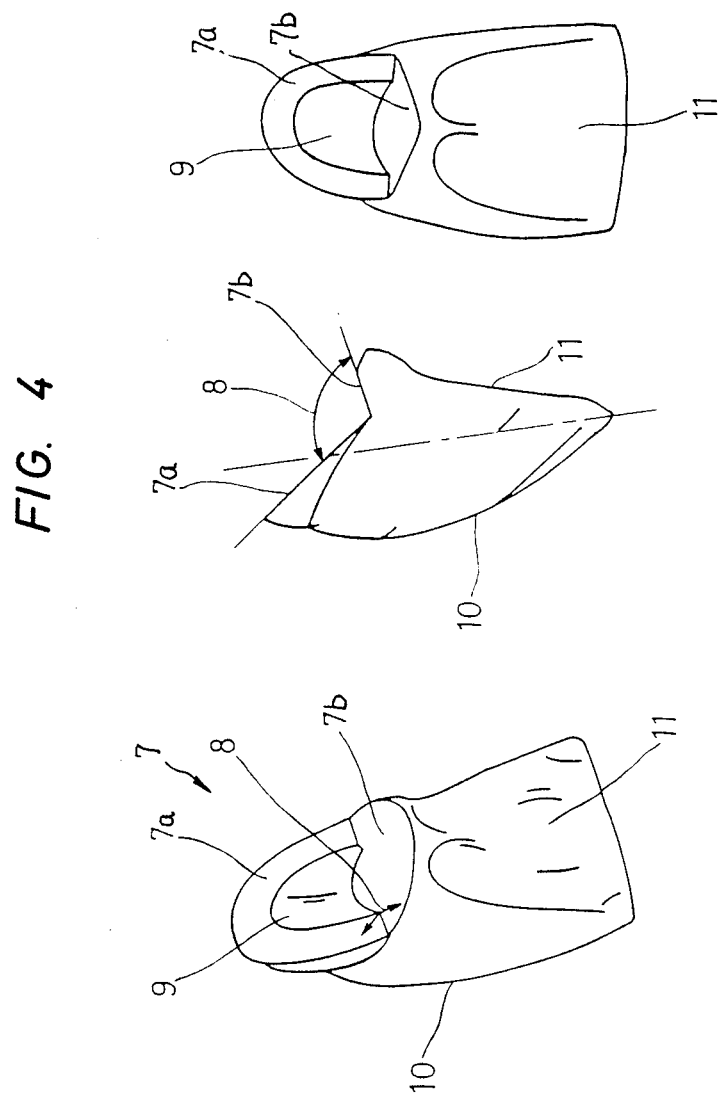
FIG. 4 illustrates the maxillary left-middle incisor of the artificial teeth for a front-tooth portion according to the present invention.

Reference will now be made to the means for solving the problems as stated in the foregoing.

(1) In the preparation of a denture, the angle of retention of an artificial tooth is effective for the prevention of its disengagement incidental to fracturing of gypsum, when gypsum-indexing with a gypsum clamp. This is because a force acting from one direction is maintained, while dispersed into two tensile and shearing forces.

(2) Complicated movements effected by mastication in the mouth are three-dimensionally broken down into lateral, anterior/prosterior and vertical movements. Such movements define a repeated load which in turn gives rise to fatigue. However, the angle of retention permits a force exerted by them to be dispersed throughout the basal plane, abaiting fatigue breakage due to the repeated load.

(3) When carrying out occlusal equilibration during the repair of a denture, a polishing point causes fine vibrations, leading to cracking of the interface of the basal plane of an artificial tooth and a plate resin. According to the present invention, however, the angle of retention of the basal plane serves effectively to prevent such cracking. As is the case with (2), this implies that the angle of retention assumes a shape that can reduce as much stress concentration on that interface as possible by resistance to a repeated load.

(4) The disengagement of an artificial tooth due to a patient's mishandling depends upon how an impact force is dispersed over the basal plane. The angle of retention of the basal plane according to the present invention serves effectively to disperse this force. On the same principle as in (1), therefore, the artificial tooth having an angle of retention can maintain the impact force while being dispersed into both tensile and shearing forces, resulting in improvements in bond toughness.

(5) When trying the selected artificial tooth implanted in a temporary fitting wax in the mouth, the angle of retention permits the artificial tooth to be easily implanted in the wax without slippage, and keeps the artificial tooth in place. Thus, it is possible to prevent the artificial tooth from dropping into the patient's mouth during try-in and, hence, considerably abates the fear that the patient's throat or bronchus may be clogged up by the dropped artificial tooth, leading to suffocation.

According to the present invention, the angle of retention of the basal plane surface of the artificial tooth assumes a cancave shape and should preferably be equal to or layer than 45° and less than 180°. At an eagle of retention of below 45°, stress concentrates upon a portion forming the angle of retention in a similar manner as experienced with a notch, and brings about breaking of the artificial tooth itself. In addition, such a small angle poses an appearance problem, since the plate resin is exposed to open view, when seen from the adjacent side. At an angle of retention exceeding 180°, there is a sharp decrease in the resistances to shocks, fatigue due to repeated loads and cracking due to fine vibrations. In addition, such a large angle makes it difficult to implant the selected artificial tooth in a temporal fitting wax for a try-in-the-mouth operation, and results in the fear that the disengagement of the artificial tooth may occur in the mouth. If a retaining hole is provided, the retaining hole should preferably assume a gentle concave shape without any undercut. Not only retaining holes provided with undercuts vary in quality but also, as is the case with holes having angular planes, they form a notch with a plate resin. Stress concentrations on that notch present a major cause of fracturing on the plate resin portion.

The geometry of the basal plane surface according to the present invention may be made to accommodative either a front-tooth portion or a molar-tooth portion. In particular, the effect that the angle of retention has on the molar-tooth portion becomes more important, since its cusps or clefts have to be frequently polished for occlusal equilibration.

The artificial teeth according to the present invention may be formed of a synthetic resin or a composite material of synthetic resins and ceramics. The synthetic resins to be used may include methyl methacylate, ethyl methacrylate, isopropyl methacrylate, hydroxyethyl methacrylate, tetrahydrofurfuryl methacrylate, glycidyl methacrylate, 2,2-bis(methacryloxyphenyl) propane, 2,2-[4-(2-hydroxy-3-methacryloxyphenyl)] propane, 2,2-bis(4-methacryloxyethoxyphenyl) propane, 2,2-bis(4-methacryloxydiethoxyphenyl) propane, 2,2-bis(4-methacryloxypropoxyphenyl) propane, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol trimethacrylate, trimethylolmethane trimethacrylate and pentaerythritol tetramethacrylate as well as acrylates analogous thereto. These resins may be used alone or in combination or crosslinked form, and are all polymerized with an organic peroxide such as benzoyl peroxide or an azo compound such as azobisisobutyronitrile for use.

The ceramics for making the enamel portion composite with the synthetic resins may include powdered quartz, powdered alumina, powdered glass, kaolin, talc, calcium carbonate, barium aluminosilicate glass, titanium oxide, borosilicate glass, powdered colloidal silica, a so-called organic composite filler obtained by compacting colloidal silica with a polymer followed by pulverization, alumina whisker, beryllium oxide whisker, boron carbide whisker, silicon carbide whisker, silicon nitride whisker, various metal whiskers (chromium, copper, iron, nickel and the like) or anything similar thereto. These ceramics may preferably be treated by coupling to increase their bond strength with respect to the synthetic resin providing a binder resin. The coupling agents to be used may include organofunctional silane coupling agents, titanate coupling agents and aluminate coupling agents by way of example. The ceramics may be grafted on their surfaces to increase their bond strength with respect to the binder resin.

EXAMPLES

The present invention will now be explained specifically but not exclusively with reference to the examples and comparative examples.

EXAMPLES 1 THROUGH 14

The properties of the artificial teeth according to the present invention are summarized in the following table.

COMPARATIVE EXAMPLES 1 THROUGH 10

These were carried out to restrict the scope of the examples. The resulting properties are shown in the following table.

TABLE

| | Artificial Teeth | Materials | Retaining Angles (Degree) | Retaining Holes | Impact Bond Test No. of Teeth Disengaged/ No. of Tests | Resin Test-Bonding (JDMAS) kgf (Standard Deviation) | Geometry of Artificial Teeth or Brandname |
|---|---|---|---|---|---|---|---|
| Example 1 | Front Tooth | Artificial Resin | 120 | Concave Shape with No Undercut | 0/10 | 29.7 (6.97) | Maxillary Left-middle Incisor of Artificial Tooth VT6 |
| Example 2 | Front Tooth | Artificial Resin | 60 | Concave Shape with No Undercut | 0/10 | 22.1 (4.53) | Maxillary Left-middle Incisor of Artificial Tooth VT6 |
| Example 3 | Front Tooth | Artificial Resin | 90 | Concave Shape with No Undercut | 0/10 | 29.6 (2.87) | Maxillary Left-middle Incisor of Artificial Tooth VT6 |
| Example 4 | Front Tooth | Artificial Resin | 150 | Concave Shape with No Undercut | 0/10 | 22.3 (6.53) | Maxillary Left-middle Incisor of Artificial Tooth VT6 |
| Example 5 | Front Tooth | Artificial Resin | 170 | Concave Shape with No Undercut | 2/10 | 20.8 (11.01) | Maxillary Left-middle Incisor of Artificial Tooth VT6 |
| Example 6 | Molar Tooth | Artificial Resin | 120 | Concave Shape with No Undercut | 0/10 | 36.3 (4.26) | Maxillary Left-primary Molar Tooth 30M |
| Example 7 | Molar Tooth | Artificial Resin | 60 | Concave Shape with No Undercut | 0/10 | 30.3 (1.23) | Maxillary Left-primary Molar Tooth 30M |
| Example 8 | Molar Tooth | Artificial Resin | 90 | Concave Shape with No Undercut | 0/10 | 21.6 (9.85) | Maxillary Left-primary Molar Tooth 30M |
| Example 9 | Molar Tooth | Artificial Resin | 150 | Concave Shape with No Undercut | 0/10 | 20.7 (7.35) | Maxillary Left-primary Molar Tooth 30M |
| Example 10 | Molar Tooth | Artificial Resin | 170 | Concave Shape with No Undercut | 0/10 | 24.6 (2.41) | Maxillary Left-primary Molar Tooth 30M |
| Example 11 | Front Tooth | Composite Material Only for Enamel | 120 | Concave Shape with No Undercut | 0/10 | 22.0 (3.62) | Maxillary Left-middle Incisor of Artificial Tooth VT6 |
| Example 12 | Molar Tooth | Composite Material Only for Enamel | 120 | Concave Shape with No Undercut | 0/10 | 28.9 (2.08) | Maxillary Left-primary Molar Tooth 30M |
| Example 13 | Front Tooth | Artificial Resin | 120 | Without Retaining Holes | 0/10 | 20.0 (5.44) | Maxillary Left-middle Incisor of Artificial Tooth VT6 |
| Example 14 | Molar Tooth | Artificial Resin | 120 | Without Retaining Holes | 0/10 | 25.6 (2.20) | Maxillary Left-primary Molar Tooth 30M |
| Comparative Example 1 | Front Tooth | Artificial Resin | 180 | Without Retaining Holes | 3/10 | 16.7 (2.98) | Ribdent Plastic Resin VT6 Manufactured by G-C Maxillary Left-middle Incisor of Artificial Tooth |
| Comparative Example 2 | Front Tooth | Artificial Resin | 180 | Concave Shape with No Undercut | 3/10 | 18.9 (4.90) | Maxillary Left-middle Incisor of Artificial Tooth VT6 |
| Comparative Example 3 | Front Tooth | Artificial Resin | 30 | Concave Shape with No Undercut | 8/10 | 9.5 (2.74) | Maxillary Left-middle Incisor of Artificial Tooth VT6 |
| Comparative Example 4 | Front Tooth | Artificial Resin | 270 | Concave Shape with No Undercut | 5/10 | 12.0 (2.65) | Maxillary Left-middle Incisor of Artificial Tooth VT6 |
| Comparative Example 5 | Molar Tooth | Artificial Resin | 180 | Without Retaining Holes | 3/10 | 20.6 (0.79) | Ribdent FB-20, 30 Manufactured by G-C Maxillary Left-primary Molar Tooth |
| Comparative Example 6 | Molar Tooth | Artificial Resin | 180 | Concave Shape with No Undercut | 1/10 | 15.9 (7.30) | Maxillary Left-primary Molar Tooth 30M |
| Comparative Example 7 | Molar Tooth | Artificial Resin | 30 | Concave Shape with No Undercut | 1/10 | 19.5 (6.80) | Maxillary Left-primary Molar Tooth 30M |
| Comparative | Molar Tooth | Artificial | 270 | Concave Shape | 1/10 | 17.9 (1.96) | Maxillary Left-primary |

TABLE-continued

| | Artificial Teeth | Materials | Retaining Angles (Degree) | Retaining Holes | Impact Bond Test No. of Teeth Disengaged/ No. of Tests | Resin Test-Bonding (JDMAS) kgf (Standard Deviation) | Geometry of Artificial Teeth or Brandname |
|---|---|---|---|---|---|---|---|
| Example 8 | | Resin | | with No Undercut | | | Molar Tooth 30M |
| Comparative Example 9 | Front Tooth | Composite Material Only for Enamel | 180 | Concave Shape with No Undercut | 5/10 | 11.8 (1.73) | Maxillary Left-middle Incisor of Artificial Tooth VT6 |
| Comparative Example 10 | Molar Tooth | Composite Material Only for Enamel | 180 | Concave Shape with No Undercut | 3/10 | 19.2 (0.96) | Maxillary Left-primary Molar Tooth 30M |

Tests for the bonding between the plate resins and the artificial teeth were carried out according to "Resin Teeth - Bonding" provided in Japan Dental Materials Association Standards (JDMAS). According to the procedures described therein, an artificial tooth to be tested is implanted in a wax model shown in FIG. 1 which illustrates a test sample fixing jig 1, artificial tooth 2 and denture base resin 3, while a line connecting its apex with its cervix forms an angle of 45° with a center axis of the wax model, and is invested with gypsum in a polymerization flask. Then, the wax is removed and discharged with hot water. After applying a resin-gypsum releasing material on a gypsum surface, a plate material (Acron manufactured by G-C in the present invention) according to JIS T 6501 (Acrylic resins for Dental Plates) is placed on and brought into pressure contact with that surface, followed by 60 minute-heating at about 100° C. After being cooled down to room temperature, a test sample is removed and fixed in place as shown in FIG. 2, to which a force is then applied. The loading rate is about 12 kgf per minute. Impact bond tests for an artificial tooth and a plate resin were carried out in the following manner. According to "Resin Teeth - Bonding" providing in JDMAS already referred to, ten samples are prepared. Metal lumps or masses each weighing 100 g are dropped from a height of 16 cm on the artificial tooth portions of the samples to examine the number of the artificial teeth disengaged from the plates. FIG. 3 illustrates an impact bond testing jig wherein load 5 applied is a 100 g metal mass and 6 represents a 16 cm length tube for grinding load 5. FIGS. 4 and 5 illustrates typical artificial teeth according to the present invention. FIG. 4 illustrates the maxillary right-middle incisor for a front-tooth portion, and FIG. 5 shows the maxillary right-primary molar for a molar-tooth portion. In FIGS. 4 and 5, reference numerals 7a, 7c stands, respectively, for the labial and buccal subplanes of a basal plane 7, and 8, an angle that the the labial subplane 7a or the buccal subplane 7C makes with the lingual subplane 7b, i.e., an angle of retention. Reference numeral 9 indicates a retaining hole provided in the labial or buccal subplane 7a, 7c, which assumes a concave shape defined by gently curved faces and is provided with no undercut. Reference numeral 11 denotes a lingual subplane. Reference numeral 10 in FIG. 4 shows a labial subplane; and reference numerals 13 and 12 in FIG. 5 a buccal subplane and an occlusal subplane, respectively.

Examples 1 to 5, 11 and 13 are directed to the maxillary left-middle incisors of the artificial teeth for a front-tooth portion.

The artificial teeth according to Examples 1 to 5 are formed of a synthetic resin and have angles of retention of 120°, 60°, 90°, 150° and 170°. Further, such artificial teeth each include therein a retaining hole assuming a concave shape and are provided with no undercut. The bond strength of the teeth with respect to the plate resin reached a highest angle of 120° and dropped to a lowest angle of 170°. In each run of impact bond testing, all the samples showed zero except two samples having an angle of retention of 170°.

The artificial tooth according to Example 11 has its enamel formed of a composite synthetic resin/ceramic material and has an angle of retention of 120°. Satisfactory results were obtained in terms of both bond strength with respect to the plate resin and impact bond testing.

The artificial tooth according to Example 13 is formed of a synthetic resin, includes therein no retaining hole, and has an angle of retention of 120°. Favorable results were obtained in terms of both bond strength with respect to the plate resin and impact bond testing.

Examples 6 to 10, 12 and 14 are directed to the maxillary left-primary molars of the artificial teeth for a molar-tooth portion. The artificial teeth according to Examples 6 to 10 are formed of a synthetic resin and have angles of retention of 120°, 60°, 90°, 150° and 170°. The obtained bond strength values are generally larger than those for a front-tooth portion for the reason that the areas of the basal planes are larger than those of the front teeth. In the impact bond test, the number of the artificial teeth that disengaged from the plates were zero.

The artificial tooth according to Example 12 has its enamel formed of a composite synthetic resin/ceramic material and has an angle of retention of 120°. Satisfactory results were obtained in terms of both bond testing (JDMAS) and impact bond testing.

The artificial tooth according to Example 14 is formed of a synthetic resin, includes therein no retaining hole, and has its angle of retention of 120°. Favorable results were obtained in terms of both the bond strength with respect to the plate resin and the impact bond testing.

Comparative Examples 1 to 4 and 9 are directed to the maxillary left-middle incisors of the artificial teeth for a front-tooth portion.

The artificial teeth of Comparative Examples 1 to 4 are formed of a synthetic resin, and the artificial tooth of Comparative Example 9 has only its enamel formed of a composite synthetic resin/ceramic material.

Comparative Example 1 is directed to the maxillary left-middle incisor of the Ribdent Plastic Resin Teeth VT6 manufactured by G-C, and has an angle of retention of 180° and is provided with no retaining hole.

In Comparative Examples 2 and 4 the artificial teeth have angles of retention larger than the upper limit defined in the appended claims and, in Comparative Example 3, the artificial tooth has an angle of retention smaller than the lower limit defined in the appended claims. These artificial teeth are all inferior to those of Examples 1 to 5 in terms of the impact bond testing and the bond testing (JDMAS).

In Comparative Example 9, the artificial tooth has its enamel formed of a composite synthetic resin/ceramic material, and has an angle of retention of 180°. This is inferior to the artificial teeth of Example 11 in terms of the impact bond testing and the bond testing (JDMAS).

Comparative Examples 5 to 8 and 10 are directed to the maxillary left-primary molar teeth of the artificial teeth for a molar-tooth portion. In Comparative Examples 5 to 8, the artificial teeth are formed of a synthetic resin and in Comparative Example 10, the artificial tooth has only its enamel formed of a composite synthetic resin/ceramic material.

Comparative Example 5 is directed to the maxillary left-primary molar tooth formed of Ribdent FB-20 and 30M manufactured by G-C.

In Comparative Examples 6 and 8, the angles of retention are larger than the upper limit defined in the appended claims and, in Comparative Example 7, the angle of retention is smaller than the lower limit defined in the appended claims. These are all inferior to the artificial teeth of Examples 6 to 10 in terms of the impact bond testing and the bond testing (JDMAS). The artificial tooth of Comparative Example 10 has its enamel formed of a composite synthetic resin/ceramic material, has its angle of retention of 180°, and is inferior to that of Example 12 in terms of both the impact bond testing and the bond testing (JDMAS).

The artificial teeth according to the present invention are provided on their basal planes with an angle of retention equal to or larger than 45° and less than 180°, and are characterized by the following points.

(1) When preparing a denture with the use of the artificial teeth having an angle of retention, there is no fear that the artificial teeth may be disengaged from the plate resin. This is because the angles of retention serve effectively to disperse a force tending to disengage the artificial teeth from the plate into a simple tensile force and a shearing force.

(2) When actually used in the mouth, the denture undergoes complicated mastication movement, i.e., lateral, anterior/prosterior and vertical movements. The repetition and accummulation of such movements lead to fatigue fracturing of the interface. With the artificial teeth having an angle of retention, however, such repeated loads are dispersed throughout their basal planes, thereby contributing to keeping the artificial teeth in place.

(3) In some cases, the cusps of the artificial teeth are polished with a carbon random point for occlusal equilibration at the time of the repair of a denture. The fine vibrations then generated cause cracking to occur on the interface of the artificial teeth and the plate resin. The angles of retention serve effectively to prevent the progress of such cracking.

(4) Inadvertant disengagement of the artificial teeth from the plate is caused by patient's mishandling such as dropping or treading on them. In this case, an impact force is applied to the denture whereby the artificial teeth are disengaged from the plate. However, the impact bond strength of the artificial teeth of the present invention with respect to the plate increasingly improved by their specific basal planes having an angle of retention.

(5) When trying the selected artificial teeth implanted in a temporal fitting wax in the mouth, the angles of retention make it easy to implant the artificial teeth without slippage, and eliminate the possibility of the disengagement of artificial teeth in the mouth, thus considerably abaiting danger to patients.

What is claimed is:

1. An artificial tooth having a basal plane in which an areal ration of one of a labial and a buccal subplane to a lingual subplane is in a range of 10:1 to 1:10, and wherein an angle of retention between said one of said labial and buccal subplanes and the lingual subplane is equal to or larger than 45° and less than 180° and wherein a retaining hole is provided in said one of said labial and buccal subplanes.

2. An artificial tooth as claimed in claim 1, wherein said retaining hole provided therein assumes a concave shape defined by gently curved faces, and is provided with no undercut.

3. An artificial tooth as claimed in claim 2, which is accommodative to a front-tooth portion.

4. An artificial tooth as claimed in claim 3, which is formed of a synthetic resin.

5. An artificial tooth as claimed in claim 3, which is formed of a composite material of synthetic resins and ceramics.

6. An artificial tooth as claimed in claim 2, which is accommodative to a molar-tooth portion.

7. An artificial tooth as claimed in claim 6, which is formed of a synthetic resin.

8. An artificial tooth as claimed in claim 6, which is formed of a composite material of synthetic resins and ceramics.

9. An artificial tooth as claimed in claim 2, which is formed of a synthetic resin.

10. An artificial tooth as claimed in claim 2, which is formed of a composite material of synthetic resins and ceramics.

11. An artificial tooth as claimed in claim 1, which is accommodative to a front-tooth portion.

12. An artificial tooth as claimed in claim 11, which is formed of a synthetic resin.

13. An artificial tooth as claimed in claim 11, which is formed of a composite material of synthetic resins and ceramics.

14. An artificial tooth as claimed in claim 1, which is accommodative to a molar-tooth portion.

15. An artificial tooth as claimed in claim 14, which is formed of a synthetic resin.

16. An artificial tooth as claimed in claim 14, which is formed of a composite material of synthetic resins and ceramics.

17. An artificial tooth as claimed in claim 1, which is formed of a synthetic resin.

18. An artificial tooth as claimed in claim 1, which is formed of a composite material of synthetic resins and ceramics.

* * * * *